United States Patent [19]

Johnston et al.

[11] Patent Number: 5,166,201
[45] Date of Patent: Nov. 24, 1992

[54] 2β,19-ETHYLENE BRIDGED STEROIDS AS AROMATASE INHIBITORS

[75] Inventors: J. O'Neal Johnston, Milford; Norton P. Peet, Cincinnati; Joseph P. Burkhart, West Chester, all of Ohio

[73] Assignee: Merrell Dow Pharmaceuticals Inc., Cincinnati, Ohio

[21] Appl. No.: 621,184

[22] Filed: Nov. 30, 1990

[51] Int. Cl.$^5$ .................... A61K 31/565; C07J 53/00
[52] U.S. Cl. .................... 514/177; 514/178; 514/182; 552/510
[58] Field of Search .................... 514/177, 178, 182; 552/510; 435/184

[56] References Cited

U.S. PATENT DOCUMENTS 4,322,416 3/1982 Metcalf et al. .................... 514/177
4,902,717 2/1990 Senior et al. .................... 514/562

FOREIGN PATENT DOCUMENTS 42-1754 1/1967 Japan .................... 552/510

OTHER PUBLICATIONS

Eggleston et al. Chemical Abstracts, vol. 109, 1988 Abstract 139666j.
Johnston et al., Endocrinology 115(2), 1984 pp. 776-785.
Lan-Hargest et al. Tetrahedron Letters, 28 (49) pp. 6117-6120, 1987.
Greway et al., *Biochemistry International*, 20, 591 (1990).
Burkhart et al., *Steroids* 45:357, 1985.

Primary Examiner—Robert T. Bond
Assistant Examiner—E. C. Ward
Attorney, Agent, or Firm—John J. Kolano

[57] ABSTRACT

The present invention is directed to a group of androstane compounds which contain an ethylene radical bridging the 2- and 19-positions. These compounds are useful as aromatase inhibitors and they are prepared by the cyclization of a 19-[2-(4-toluenesulfonyloxy)ethyl]androst-4-ene-3,17-dione using a strong base.

12 Claims, No Drawings

2β,19-ETHYLENE BRIDGED STEROIDS AS AROMATASE INHIBITORS

BACKGROUND OF THE INVENTION

The estrogen hormones, estrone and estradiol, are involved in many physiological processes. The formation of these steroids is regulated by a number of enzymes. The enzyme aromatase is the rate limiting enzyme in the nonreversible conversion of the androgen hormones, testosterone and androstenedione, to the estrogen hormones, estradiol and estrone. Compounds which are aromatase inhibitors can thus regulate or inhibit androgen to estrogen conversion, and have therapeutic utility in treating clinical conditions potentiated by the presence of estrogens.

DETAILED DESCRIPTION OF THE INVENTION

The present invention is directed to 2,19-ethylene bridged steroid compounds which are steroidal aromatase inhibitors, their related intermediates, their use as aromatase inhibitors, and the process for their preparation. More specifically, the compounds of this invention are represented by the following structure:

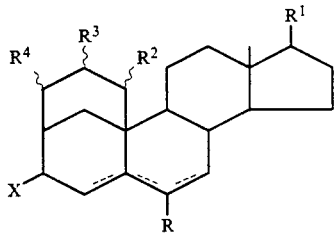

wherein
===== represents a single or double bond;
R is H, =CH$_2$, =O, or —OH;
R$^1$ is =O, —OH, or —O—(C$_{1-4}$ alkanoyl);
R$^2$, R$^3$ and R$^4$ are each independently H or C$_{1-4}$ alkyl; and
X is =O, =CH$_2$, —OH, or —O—(C$_{1-4}$ alkanoyl).

The C$_{1-4}$ alkyl groups referred to above can be exemplified by methyl, ethyl and propyl. The C$_{1-4}$ alkanoyl groups referred to above can be exemplified by formyl, acetyl, propionyl and butyryl. In those cases where X, R and R$^1$ are monovalent groups, those groups have the β-configuration with respect to the steroid molecule and hydrogen is additionally present at the same position and the hydrogen has the α-configuration with respect to the steroid molecule. The wavy lines to the groups R$^2$, R$^3$ and R$^4$ indicate that those groups can have either of the stereochemical configurations which are possible with the other substituent at that ring position being hydrogen. The double bonds as shown by the dotted lines are limited to the extent that it is not possible to have two double bonds extending from the same carbon atom and a double bond is possible at the 6-position only when there is also a double bond at the 4-position. In addition, the compound must contain at least one double bond either at the 4- or the 5-position.

In describing the compounds of the present invention, they have been referred to generally as 2β,19-ethylene bridged steroids and similar terminology is used below in naming some of the specific compounds encompassed by the present invention. This terminology indicates that there is a two-carbon chain which has two free valences but on different carbon atoms and which connects the 2- and 19-positions in a regular steroid molecule. The β-designation is further used in connection with the 2-position to provide an explicit indication that the bridge is attached there on the β-face.

Some specific examples of compounds of the present invention are the following:
2β,19-(Ethylene)androst-4-ene-3,17-dione.
2β,19-(Ethylene)androsta-4,6-diene-3,17-dione.
2β,19-(Ethylene)androst-5-ene-3β,17β-diol.
2β,19-(Ethylene)androst-5-ene-3β,17β-diol diacetate.
2β,19-Ethylene-6-methyleneandrost-4-ene-3,17-dione.
2β,19-(Ethylene)androst-4-ene-3,6,17-trione.
2β,19-Ethylene-6β-hydroxyandrost-4-ene-3,17-dione.
2β,19-Ethylene-19-methylandrost-4-ene-3,17-dione The compounds of the present invention can be obtained by the internal cyclization of a 19-substituted steroid having an appropriately positioned leaving group on that 19-substituent. More particularly, the compounds of the present invention are prepared by the reaction of a steroid having the following structure:

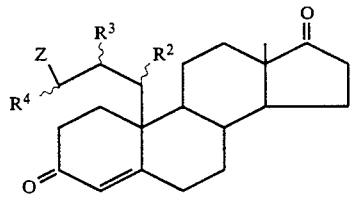

wherein R$^2$, R$^3$ and R$^4$ are defined as above and Z is a leaving group, with a strong base in an inert solvent, with cooling. A preferred base for this reaction is lithium hexamethyldisilazide while a preferred solvent is tetrahydrofuran. Z can be any facile leaving groups although sulfonate esters are preferred and the 4-toluenesulfonate ester is particularly preferred.

The indicated process gives the corresponding product which has the same steroid nucleus but with a 2β,19-ethylene bridge. This compound can then be used to prepare other compounds of the present invention. Specifically, these further transformations will be discussed below as they would apply to the compound 2β,19-(ethylene)androst-4-ene-3,17-dione although they can also be applied to other similar compounds.

Thus, treatment of 2β,19-(ethylene)androst-4-ene-3,17-dione with chloranil in t-butanol gives the corresponding 4,6-diene, while reaction of 2β,19-(ethyleneandrose-4-ene-3,17-dione with formaldehyde acetal gives the corresponding 6-methylene compound. For the latter conversion, reagents such as p-toluenesulfonic acid, strong mineral acids, acidic ion exchange resin or, preferably, phosphoryl chloride with formaldehyde dimethyl or diethyl acetal, are most suitable.

If 2β,19-(ethylene)-androst-4-ene-3,17-dione is reduced with sodium borohydride in ethanol, the corresponding Δ$^4$-3β,17β-diol is obtained. To obtain the Δ$^5$-3β,17β-diol, the 2β,19-(ethylene)androst-4-ene-3,17-dione is first converted to the corresponding 3-acetoxy-3,5-diene. This conversion is accomplished by treating the dione with acetic anhydride in the presence of a catalytic amount of an acid such as p-toluenesulfonic acid followed by the addition of pyridine, or the conversion can be accomplished by reacting the dione with an excess of acetic anhydride and a catalytic amount of 70% aqueous perchloric acid using ethyl acetate as the solvent followed by neutralization with sodium carbonate. The 3-acetoxy-3,5-diene is then treated with calcium borohydride in ethanol at −15° C. to give the desired Δ⁵-diol. Subsequent treatment of the diol with an anhydride, such as acetic anhydride, gives the corresponding diacetate.

When 2β,19-(ethylene)androst-4-ene-3,17-dione is reacted with an excess of ethylene glycol in the presence of a catalytic amount of an acid such as methanesulfonic acid, the corresponding 3,17-bis ethylene ketal is obtained with the double bond shifting to the 5-position. Oxidation of the 5-ene with m-chloroperbenzoic acid in dichloromethane at 0° C. gives the corresponding 5,6-epoxide. Reaction of this epoxide with perchloric acid in aqueous tetrahydrofuran gives the 5,6-diol and, at the same time, the ketals are removed to leave the free 3,17-diketone. Oxidation of the diol with Jones reagent gives the corresponding 5-hydroxy-6-ketone (actually, 5-hydroxy-3,6,17-trione) which is then dehydrated using p-toluenesulfonic acid to give the Δ⁴-3,6,17-trione.

The initial bis ketal obtained in the preceding paragraph can also be used in a different synthesis. Thus, it can be selectively hydrolyzed to the corresponding 17-ketone use 0.15% aqueous perchloric acid in t-butanol and dichloromethane. The 17-ketone is then reduced with an excess of sodium borohydride in ethanol at 0° C. to give the corresponding 17β-hydroxy compound. Treatment of this alcohol with aqueous hydrochloric acid removes the 3-ketal protecting group to leave the free 3-ketone. Alternatively, the 3-keto-17β-hydroxy compound can be obtained by the selective reduction of the 3,17-diketone using lithium tri(t-butoxy)aluminum hydride. This 3-ketone is then reacted with methylenetriphenylphosphorane to give the corresponding 3-methylene-17-hydroxy compound. This is then oxidized with Jones reagent to give the desired 3-methylene-17-ketone.

The specific starting material referred to above for the preparation of 2β,19-(ethylene)androst-4-ene-3,17-dione can be obtained by the following series of reactions starting with 3,3,17,17-bis(ethylenedioxy)androst-5-ene-19-al. A Wittig reaction is used with this compound to add a two-carbon chain at the 19-position. Specifically, the indicated 19-aldehyde is treated with triethyl phosphonoacetate and a strong base such as potassium hexamethyldisilazide in an inert solvent such as tetrahydrofuran. The reaction is further carried out in the presence of a cyclic polyether such as 18-crown-6 under an inert atmosphere. Extended heating at reflux is used to ensure completion of the reaction. In addition, repeated treatments with phosphonoacetate and base may be used to ensure complete reaction. The specific product obtained by this reaction is the compound in which the 19-oxo has been replaced by a 19-[(ethoxycarbonyl)methylene] group.

The double bond in the side chain is then selectively reduced by treatment of the compound with magnesium in methanol. Trans-esterification also takes place and the reduced product is 3,3,17,17-bis(ethylenedioxy)-19-[(methoxycarbonyl)methyl]-androst-5-ene. Reduction of the ester group with a hydride reducing agent such as lithium aluminum hydride in an inert solvent such as ethyl ether gives the corresponding 19-(2-hydroxyethyl) compound which is then reacted with an appropriate reagent such as p-toluenesulfonyl chloride in pyridine to give the corresponding ester. Other leaving groups can be introduced by standard procedures. The ethylene ketal groups are then removed by standard procedures such as treatment with p-toluenesulfonic acid in acetone. This gives the desired 3,17-dione intermediate.

Intermediates for the compounds in which $R^4$ is $C_{1-4}$ alkyl can be obtained by using some of the same intermediates referred to in the preceding paragraph. Thus, the 19-[(methoxycarbonyl)methyl] compound can be reduced using diisobutylaluminum hydride in toluene to give 3,3,17,17-bis(ethylenedioxy)-19-(2-oxoethyl)androst-5-ene. Alternatively, this 19-(2-oxoethyl) compound can be obtained by the oxidation of the corresponding 19-(2-hydroxyethyl) compound using oxalyl chloride and dimethyl sulfoxide followed by triethylamine. The oxo compound is then reacted with the appropriate alkyl lithium or alkyl Grignard in tetrahydrofuran to give the corresponding 19-(2-alkyl-2-hydroxyethyl) compound. This alcohol is then converted to the corresponding p-toluenesulfonate ester and the ethylene ketal protecting groups are removed as indicated in the preceding paragraph.

The compounds of the present invention are inhibitors of aromatase. As aromatase inhibitors, they are useful in treating hyperestrogenemia. The compounds are useful in controlling abnormally high levels of estrogens, both when the high levels observed are relatively steady, or when there are brief surges of elevated levels occurring as part of cyclical neuroendocrine functions. Both females and males can be treated, although obviously, the level of estrogens which would be considered high in males would be much lower than the amount considered high in females. These compounds are also useful as anti-fertility aqents to prevent ovulation or implantation in females, or to reduce the mating behavior in males where brain aromatization is required for such behavior. These compounds further have value in treating gynecomastia, male infertility resulting from elevated estrogen levels, and hyperestrogenemia, which may precede myocardial infarction. The compounds also may be used to treat breast cancer and other various estrogen-induced or estrogen-stimulated tumors and hyperplastic tissue disorders.

To achieve their desired effect, the compounds of the present invention may be administered orally, parenterally, for example, intravenously, intraperitoneally, intramuscularly, or subcutaneously, including the injection of the active ingredient directly into tissue or tumor sites, to a patient in need of treatment. The term patient is taken to mean a warm-blooded animal, for example, mammals such as humans, primates, cattle, dogs, cats, horses, sheep, mice, rats and pigs. These compounds may also be administered in the form of a pharmaceutical preparation, and may further be incorporated into sustained delivery devices. The amount of compound administered will vary over a wide range and be any effective amount. Depending on the patient to be treated, the condition to be treated, and mode of administration, the effective amount of compound administered will vary from about 0.01 to 150 mg/kg of body weight per day, and preferably from about 0.1 to 50 mg/kg body weight per day.

For oral administration, the compounds can be formulated into solid or liquid preparations, such as capsules, pills, tablets, troches, powders, solutions, suspensions, or emulsions. The solid unit dosage forms can be a capsule which can be of the ordinary gelatin type containing the active compound and a carrier, for example, lubricants and inert filler such as lactose, sucrose and corn starch. In another embodiment, an active compound of the invention can be tableted with conventional tablet bases such as lactose, sucrose and corn starch in combination with binders such as acacia, corn starch, alginic acids and a lubricant such as stearic acid or magnesium stearate.

For parenteral administration the compounds may be administered as injectable dosages of a solution or suspension of the compound in a physiological acceptable diluent with a pharmaceutical carrier which can be a sterile liquid such as water-in-oil with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general, water, saline, aqueous dextrose and related sugar solutions, ethanols and glycols, such as propylene glycol or polyethylene glycol are preferred liquid carriers, particularly for injectable solutions.

The compounds can be administered in the form of a cutaneous patch, a depot injection, or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones, for example, Silastic ®, silicone rubber manufactured by Dow Corning Corporation. Further information on suitable pharmaceutical carriers and formulation techniques are found in standard texts such as *Remington's Pharmaceutical Sciences*, Mack Publishing Company, Easton, Pa.

The following are illustrative of specific pharmaceutical formulations, suitable for oral administration, which may be employed in practicing the present invention:

| TABLET | |
|---|---|
| (a) 2$\beta$,19-(Ethylene)androst-4-ene-3,17-dione | 75 g |
| (b) Lactose | 1.216 Kg |
| (c) Corn starch | 0.3 Kg |

Mix the active ingredient, the lactose and corn starch uniformly. Granulate with 10% starch paste. Dry to a moisture content of about 2.5%. Screen through a No. 12 mesh screen. Add and mix the following:

| (a) Magnesium Stearate | 0.015 Kg |
|---|---|
| (b) Corn starch qs ad | 1.725 Kg |

Compress on a suitable tablet machine to a weight of 0.115 g/tablet.

| SOFT GELATIN CAPSULE | |
|---|---|
| (a) 2$\beta$,19-(Ethylene)androst-4-ene-3,17-dione | 0.25 Kg |
| (b) Polysorbate 80 | 0.25 Kg |
| (c) Corn oil qs ad | 25.0 Kg |

Mix and fill into 50,000 soft gelatin capsules.

The activity of the present compounds in the inhibition of aromatase is demonstrated by using laboratory methods similar to procedures described in U.S. Pat. No. 4,322,416, and as published in Johnston et al., *Endocrinology* 115:776, 1984, and Burkhart et al., *Steroids* 45:357, 1985.

In this assay, the inhibitor is preincubated with enzyme prior to assaying for activity in the presence of high substrate levels. A time-related decrease in enzyme activity can be indicative of irreversible binding of a preferred method of inhibition.

In the time-dependent assay, an amount of the enzyme inhibitor in 100 $\mu$l of the assay buffer described above which will provide assay concentrations which are usually between 1 nM and 10 $\mu$m are added to 35-ml centrifuge tubes containing 600 $\mu$l of the NADPH generating system. The preincubation is started by the addition of 700 $\mu$l of aromatase preparation, usually 300–800 $\mu$g of microsomal protein per ml of assay buffer. These preparations are mixed using a vortex mixer and incubated for 0, 5, 10 or 20 minutes at 25° C. Then 100 $\mu$l of androstenedione ($-6.8$ $\mu$M) containing 1$\beta$-$^3$H androstenedione is added in assay buffer to provide an assay concentration of substrate (0.55 $\mu$M) which is at least ten times the $K_m$ of androstenedione (0.04 $\mu$M). Following vortexing, the enzyme incubation is continued for 10 minutes before being terminated by the addition of chloroform. The amount of radioactivity in the aqueous fraction is determined by scintillation procedures. The enzymatic activity for each concentration of inhibitor at each time period of preincubation is calculated as a percent of the "0" minute vehicle control arbitrarily set at 100%. Therefore, the present enzyme inhibition is expressed as a percentage: (100 percent minus percent enzyme activity with inhibitor present).

Enzyme kinetic analysis utilized Kitz-Wilson plots for time-dependent assays. These analyses provide estimates of apparent $K_i$ of inactivation which represents the inhibitor concentration required to produce half-maximal rate of enzyme inactivation. The pseudo first-order rate constant for enzyme inactivation ($k_{cat}$) and the half-time of inactivation ($\tau_{50}$) of infinite inhibitor concentrations were determined. The ratio of $k_{cat}/K_i$ (inactivation) provides an index number which increases with increased efficiency of enzyme inactivation and increased inhibitor affinity for the enzyme active site. Using this test, the following results were observed for the compound 2$\beta$,19-(ethylene)androst-4-ene-3,17-dione:

$K_i$ (nM) = 23.9

$\tau_{50}$ (min) = 0.87

$k_{cat}/K_i$ = 557,710

The following examples are presented to illustrate the present invention but they should not be construed as limiting it in any way.

EXAMPLE 1

To a stirred solution of triethyl phosphonoacetate (3.06 ml, 15.44 mmole) and 18-crown-6 (1,4,7,10,13,16-hexaoxacyclooctadecane, 5.44 g, 20.59 mmole) in tetrahydrofuran (100 ml) under argon was added potassium hexamethyldisilazide (30.88 ml of a 0.5M solution in toluene, 15.44 mmole). After 5 min, 3,3,17,17-bis(ethylenedioxy)androst-5-en-19-al (2.00 g, 5.15 mmole) was added, the reaction stirred for 30 minutes and then heated to reflux. After 89 hours at reflux, the reaction was allowed to cool to room temperature. In a separate flask, to a stirred solution of triethyl phosphonoacetate (0.51 ml, 2.57 mmole) and 18-crown-6 (0.68 g, 2.57 mmole) in tetrahydrofuran (20 ml) under argon was added potassium hexamethyldisilazide (5.14 ml of a 0.5M solution in toluene, 2.57 mmole). After 5 minutes, this solution was added via a transfer needle to the reaction and the reaction heated at reflux for an additional 46 hours. The reaction was concentrated to about ¼ the original volume on a rotary evaporator and poured into ethyl ether (250 ml)/saturated aqueous potassium chloride (250 ml). The layers were separated and the aqueous layer extracted with additional ethyl ether (50 ml). The combined organics were washed with saturated aqueous potassium carbonate (2×250 ml), dried (Na$_2$SO$_4$) and concentrated. Flash chromatography (6×15 cm silica gel column) eluting with ethyl acetate/hexane (40:60) gave 3,3,17,17-bis(ethylenedioxy)-19-[(ethoxycarbonyl)methylene]androst-5-ene (2.10 g, 89%) as a white foam.

$^1$H NMR (CDCl$_3$) δ 6.93 (d, 1H, J=15.9 Hz, α,β unsaturated vinyl), 5.78 (d, 1H, J=15.9 Hz, α,β unsaturated vinyl), 5.62–5.68 (m, 1H, vinyl), 4.16–4.27 (m, 2H, OCH$_2$), 3.79–4.02 (m, 8H, 2x OCH$_2$CH$_2$O), 1.31 (t, J=7.2 Hz, CH$_3$), 0.72 (s, 3H, 18-CH$_3$).

IR (KBr) 3434, 2976, 2944, 2876, 1718, 1642, 1306, 1288, 1180, 1104, 1042 cm$^{-1}$.

MS (CI, CH$_4$) m/z (rel intensity) 459 (MH$^+$, 100), 413 (20), 397 (14), 99 (14).

EXAMPLE 2

Magnesium turnings (4.77 g, 0.20 mole) in methanol (100 ml) were treated with a small crystal of iodine. After the color faded and gas evolution was evident, a solution of 3,3,17,17-bis(ethylenedioxy)-19-[(ethoxycarbonyl)methylene]-androst-5-ene (1.80 g, 3.92 mmole) in tetrahydrofuran (10 ml) was added. A water bath and then an ice-water bath was used to moderate the reaction. After all the magnesium turnings were gone, the reaction was concentrated to about ¼ the original volume on a rotary evaporator and ethyl ether (250 ml)/H$_2$O(300 ml) added to the concentrate. 1N hydrochloric acid (about 300 ml) was added slowly, with agitation until the pH of the aqueous layer was 4 to 5. The layers were separated, additional ethyl ether (200 ml) added to the aqueous layer and the aqueous layer acidified to pH 2 to 3 by the addition of additional 1N hydrochloric acid (about 100 ml). The layers were again separated and the combined organics washed with 0.5N hydrochloric acid (2×100 ml) followed by brine (100 ml). Drying (NA$_2$SO$_4$) and concentration gave an off-white foam (1.63 g), which an $^1$H NMR spectrum showed to be a 40:60 mixture of 3,3,17,17-bis(ethylenedioxy)-19-[(methoxycarbonyl)methyl]androst-5-ene and the methyl ester of the starting material. Three consecutive repetitions of the above procedure gave crude product containing less than 5% of the methyl ester of starting material. Flash chromatography (5×12 cm silica gel column) eluting with ethyl acetate/hexane (40:60) gave 3,3,17,17-bis(ethylenedioxy)-19-[(methoxycarbonyl)methyl]androst-5-ene (1.10 g, 63%) as a white foam.

$^1$H NMR (CDCl$_3$) δ 5.53–5.61 (m, 1H, vinyl), 3.81–4.04 (m, 8H, 2x OCH$_2$CH$_2$O), 3.67 (s, 3H, OCH$_3$), 0.89 (s, 3H, 18-CH$_3$).

IR (KBr) 3438, 2948, 2876, 1738, 1634, 1436, 1380, 1308, 1104, 1044 cm$^{-1}$.

MS (CI, CH$_4$) m/z (rel intensity) 447 (MH$^+$, 100), 415 (12), 385 (20) 99 (12). MS (EI) m/z (rel intensity) 446 (M$^+$, 28), 99 (100).

EXAMPLE 3

To a stirred solution of 3,3,17,17-bis(ethylenedioxy)-19-[(methoxycarbonyl)methyl]androst-5-ene (1.04 g, 2.33 mmole) in anhydrous ethyl ether (30 ml) under argon and cooled in an ice-water bath was added lithium aluminum hydride (0.13 g, 3.49 mmole). After 1 hour the reaction was treated with water (0.1 ml) followed by 1N sodium hydroxide (0.1 ml) and finally additional water (0.3 ml). The supernatants were decanted and concentrated to give crude product. Flash chromatography (5×10 cm silica gel column) eluting with ethyl acetate/hexane (60:40) gave 3,3,17,17-bis(ethylenedioxy)-19-(2-hydroxyethyl)androst-5-ene (0.90 g, 93%) as a white foam.

HRES calculated for C$_{25}$H$_{39}$O$_5$ (MH$^+$) 419.2797; found MH$^+$ = 419.2775; error = −5.2 ppm.

$^1$HNMR (CDCl$_3$) δ 5.51–5.57 (m, 1H, vinyl), 3.82–4.03 (m, 8H, 2x OCH$_2$CH$_2$O) 3.53–3.64 (m, 2H, CH$_2$O), 0.90 (s, 3H, 18-CH$_3$).

IR (KBr) 3440, 2944, 2874, 1632, 1378, 1308, 1104, 1048 cm$^{-1}$.

MS (CI, CH$_4$) m/z (rel intensity) 420 (27), 419 (MH$^+$, 100), 418 (12), 417 (22), 357 (30), 99 (12).

EXAMPLE 4

To a stirred solution of 3,3,17,17-bis(ethylenedioxy)-19-(2-hydroxyethyl)androst-5-ene (0.42 g, 1.00 mmole) in pyridine (10 ml) under argon was added p-toluenesulfonyl chloride (0.29 g, 1.50 mmole). After 3.5 hours, the reaction was concentrated on a rotary evaporator and the residue taken up in ethyl ether (60 ml)/water (60 ml). The layers were separated and the aqueous layer extracted with additional ethyl ether (30 ml). The combined organics were washed with 1N hydrochloric acid (30 ml), saturated aqueous sodium bicarbonate (30 ml) followed by brine (30 ml), dried (NA$_2$SO$_4$) and concentrated to give crude product. Flash chromatography (5×12 cm silica gel column) eluting with ethyl acetate/hexane (35:65) gave 3,3,17,17-bis(ethylenedioxy)-19-[2-(4-toluenesulfonyloxy)ethyl]androst-5-ene (0.34 g, 60%) as a white foam.

$^1$H NMR (CDCl$_3$) δ 7.80 and 7.36 (pr d, 4H, aryl), 5.49–5.53 (m, 1H, vinyl), 3.81–4.03 (m, 10H, 2x OCH$_2$CH$_2$O and CH$_2$O), 2.46 (s, 3H, aryl CH$_3$), 0.83 (s, 3H, 18-CH$_3$).

MS (CI,CH$_4$) m/z (rel intensity) 574 (22), 573 (MH$^+$, 60), 419 (21), 402 (26), 401 (100), 400 (16), 399 (28), 357 (21), 339 (21), 217 (23), 173 (43), 93 (17).

EXAMPLE 5

To a stirred solution of 3,3,17,17-bis(ethylenedioxy)-19-[2-(4-toluenesulfonyloxy)ethyl]androst-5-ene (0.67 g, 1.17 mmole) in acetone (25 ml) was added p-toluenesulfonic acid monohydrate (44 mg, 0.23 mmole). After 24 hours, the reaction was concentrated on a rotary evaporator, the residue dissolved in methylene chloride (3 ml) and loaded onto a column. Flash chromatography (4×12 cm silica gel column) eluting with ethyl acetate/hexane (65:35) gave 19-[2-(4-toluenesulfonyloxy)ethyl]androst-4-ene-3,17-dione (0.46 g, 81%) as a white foam.

$^1$H NMR(CDCl$_3$) δ 7.79 and 7.35 (pr d, 4H, J=8.1 Hz, aryl), 5.87 (s, 1H, vinyl), 4.03 (t, 2H, J=5.5 Hz, CH$_2$O), 2.46 (s, 3H, aryl-CH$_3$), 0.92 (s, 3H, 18-CH$_3$).

IR (KBr) 3444, 2946, 2858, 1738, 1670, 1618, 1358, 1188, 1176 cm$^{-1}$.

MS (CI, CH$_4$) m/z (rel intensity) 485 (MH$^+$, 100), 331 (17), 313 (17).

EXAMPLE 6

To a stirred solution of lithium hexamethyldisilazide (1.50 ml of a 1.0M solution in tetrahydrofuran, 1.50 mmole) in additional tetrahydrofuran (15 ml) under argon and cooled to −78° C. was added a chilled (−78° C.) solution of 19-[2-(4-toluenesulfonyloxy)ethyl]androst-4-ene-3,17-dione (242 mg, 0.50 mmole) in tetrahydrofuran (10 ml) dropwise. After 40 minutes at −78° C., the reaction was allowed to warm slowly (about 2 hours) to room temperature. After 1 hour at room temperature the reaction was poured into 0.5N hydrochloric acid (60 ml) and extracted with methylene chloride (60 ml then 30 ml). The combined organics were washed with 0.5N hydrochloric acid (60 ml), ½ saturated aqueous sodium bicarbonate (60 ml) followed by brine (50 ml). Drying (NA₂SO₄) and concentration gave crude product. Flash chromatography (2×15 cm silica gel column) eluting with ethyl acetate/hexane (45:55) gave 2β,19-(ethylene)androst-4-ene-3,17-dione (96 mg, 62%) as a white solid; mp=180°-183° C.

¹H NMR (CDCl₃) δ 6.02 (s, 1H, vinyl), 0.91 (s, 3H, 18-CH₃).

¹³C NMR (CDCl₃) δ 220.4, 202.6, 167.1, 128.1, 52.1, 51.1, 47.4, 43.1, 40.3, 38.8, 35.7, 34.6, 32.2, 31.4, 29.9, 27.3, 25.3, 21.7, 20.1, 18.8, 13.6.

IR (KBr) 3454, 2922, 2858, 1740, 1658, 1610, 1450, 1220 cm⁻¹.

MS (CI, CH₄) m/z (rel intensity) 313 (MH⁺, 100), 295 (18).

This compound has the following structure:

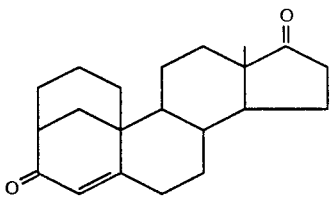

EXAMPLE 7

2β,19-(Ethylene)androst-4-ene-3,17-dione (1 mmole) is reacted with 1.3 mmoles of lithium tri-(t-butoxy)aluminum hydride (used as a 1M solution in tetrahydrofuran) in 8 ml of tetrahydrofuran at 0° C. for 45 minutes. The reaction mixture is quenched with water and then acidified with 10% hydrochloric acid. The resulting mixture is extracted with ethyl acetate and the organic extract is washed with aqueous sodium bicarbonate and brine and then dried over sodium sulfate. Evaporation of the solvent followed by chromatography gives pure 2β,19-(ethylene)-17β-hydroxyandrost-4-en-3-one.

EXAMPLE 8

To a solution of 2β,19-(ethylene)androst-4-ene-3,17-dione in t-butyl alcohol is added chloranil (1.2 equivalents). The mixture is refluxed for 3 hours, cooled, then concentrated. The residue is taken up in chloroform and washed with water, aqueous NaOH, and brine. Drying and concentration, followed by chromatography affords 2β,19-(ethylene)androst-4,6-diene-3,17-dione.

EXAMPLE 9

A suspension of sodium acetate in absolute chloroform containing formaldehyde dimethyl acetal and phosphoryl chloride is stirred at reflux for 1 hour. After addition of 2β,19-(ethylene)androst-4-ene-3,17-dione, the mixture is treated dropwise with phosphoryl chloride over a period of 2.5 hours. The reaction is subsequently stirred at reflux for the appropriate time. The suspension is allowed to cool and, under vigorous stirring, a saturated aqueous solution of sodium carbonate is added dropwise until the pH of the aqueous layer becomes alkaline, The organic layer is separated, washed with brine, and dried with sodium sulfate. After concentration and purification, the product obtained is 6-methylene-2β,19-(ethylene)androst-4-ene-3,17-dione.

What is claimed is:

1. A compound of the formula:

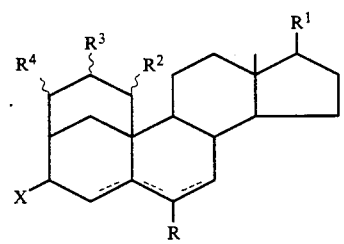

wherein

≡≡≡ represents a single or double bond;

R is H, =CH₂, =O, or —OH;

R¹ is =O, —OH, or —O—(C₁₋₄ alkanoyl);

R², R³ and R⁴ are each independently H or C₁₋₄ alkyl; and

X is =O, =CH₂, —OH, or —O—(C₁₋₄ alkanoyl).

2. A Compound according to claim 1 which has the formula:

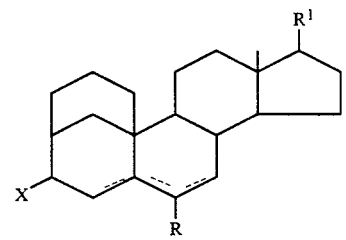

wherein

≡≡≡ represents a single or double bond;

R is H, =CH₂, =O, or —OH;

R¹ is =O, —OH, or —O—(C₁₋₄ alkanoyl); and

X is =O, =CH₂, —OH, or —O—(C₁₋₄ alkanoyl).

3. A compound according to claim 1 which has the formula:

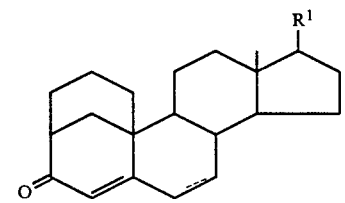

wherein

≡≡≡ represents a single or double bond; and

R¹ is =O, —OH, or —O—(C₁₋₄ alkanoyl).

4. A compound according to claim 1 which is 2β,19-(ethylene)androst-4-ene-3,17-dione.

5. A compound according to claim 1 which is 2β,19-(ethylene)-17β-hydroxyandrost-4-en-3-one.

6. A compound according to claim 1 which is 2β,19-(ethylene)-androst-4,6-diene-3,17-dione.

7. A compound according to claim 1 which is 6-methylene-2β,19-(ethylene)androst-4-ene-3,17-dione.

8. A method of inhibiting aromatase activity which comprises contacting an aromatase enzyme in vivo with an effective aromatase-inhibiting amount of a compound of the formula:

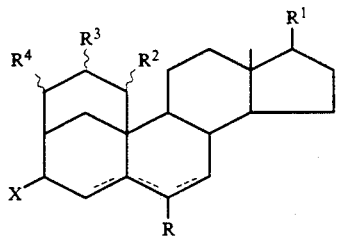

wherein
- - - - represents a single or double bond;
R is H, =CH$_2$, =O, or —OH;
R$^1$ is =O, —OH, or —O—(C$_{1-4}$ alkanoyl);
R$^2$, R$^3$ and R$^4$ are each independently H or C$_{1-4}$ alkyl; and
X is =O, =CH$_2$, —OH, or —O—(C$_{1-4}$ alkanoyl).

9. A method of treating hyperestrogenemia which comprises administering to a patient having said condition an effective aromatase-inhibiting amount of a compound of the formula:

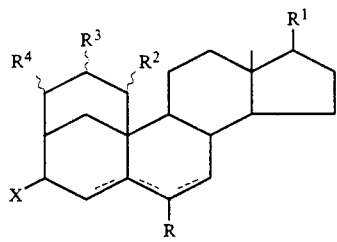

wherein
- - - - represents a single or double bond;
R is H, =CH$_2$, =O, or —OH;
R$^1$ is =O, —OH, or —O—(C$_{1-4}$ alkanoyl);
R$^2$, R$^3$ and R$^4$ are each independently H or C$_{1-4}$ alkyl; and
X is =O, =CH$_2$, —OH, or —O—(C$_{1-4}$ alkanoyl).

10. A method of treating estrogen-induced or estrogen-stimulated tumors which comprises administering to a patient having said condition an effective aromatase-inhibiting amount of a compound of the formula:

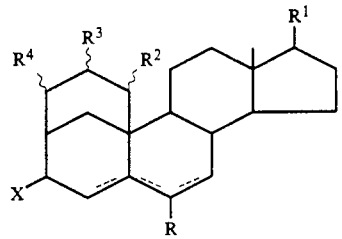

wherein
- - - - represents a single or double bond;
R is H, =CH$_2$, =O, or —OH;
R$^1$ is =O, —OH, or —O—(C$_{1-4}$ alkanoyl);
R$^2$, R$^3$ and R$^4$ are each independently H or C$_{1-4}$ alkyl; and
X is =O, =CH$_2$, —OH, or —O—(C$_{1-4}$ alkanoyl).

11. A pharmaceutical composition having aromatase inhibiting activity, in a dosage unit form, comprising a pharmaceutical carrier and a compound represented by the formula:

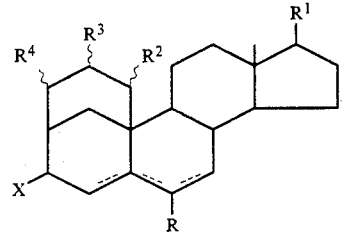

wherein
- - - - represents a single or double bond;
R is H, =CH$_2$, =O, or —OH;
R$^1$ is =O, —OH, or —O—(C$_{1-4}$ alkanoyl);
R$^2$, R$^3$ and R$^4$ are each independently H or C$_{1-4}$ alkyl; and
X is =O, =CH$_2$, —OH, or —O—(C$_{1-4}$ alkanoyl).

12. A composition according to claim 11 in which the compound is 2β,19-(ethylene)androst-4-ene-3,17-dione.

* * * * *

UNITED STATES PATENT AND TRADEMARK OFFICE
CERTIFICATE OF CORRECTION

PATENT NO. : 5,166,201

DATED : Nov. 24, 1992

INVENTOR(S) : J. O'Neal Johnston, Norton P. Peet and Joseph P. Burkhart

It is certified that error appears in the above-identified patent and that said Letters Patent is hereby corrected as shown below:

Column 2, line 50 of the patent reads "(ethyleneandrose-4" and should read --(ethylene)androst--4--.

Signed and Sealed this

Sixteenth Day of August, 1994

Attest:

BRUCE LEHMAN

Attesting Officer       Commissioner of Patents and Trademarks